United States Patent
Sugiyama et al.

(10) Patent No.: US 9,347,966 B2
(45) Date of Patent: May 24, 2016

(54) AUTOMATIC ANALYZER

(75) Inventors: Chie Sugiyama, Mito (JP); Shigeki Matsubara, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 396 days.

(21) Appl. No.: 12/867,795

(22) PCT Filed: May 1, 2009

(86) PCT No.: PCT/JP2009/058589
§ 371 (c)(1),
(2), (4) Date: Sep. 20, 2010

(87) PCT Pub. No.: WO2009/136612
PCT Pub. Date: Nov. 12, 2009

(65) Prior Publication Data
US 2011/0020949 A1    Jan. 27, 2011

(30) Foreign Application Priority Data
May 8, 2008    (JP) .................................. 2008-121768

(51) Int. Cl.
  *G01N 1/38*    (2006.01)
  *B01F 11/02*   (2006.01)
  *G01N 35/10*   (2006.01)
  (Continued)

(52) U.S. Cl.
  CPC ............. *G01N 35/1002* (2013.01); *B01F 7/161* (2013.01); *B01F 11/0283* (2013.01); *B01F 15/00253* (2013.01); *B01F 15/00435* (2013.01); *B01F 2015/00629* (2013.01); *B01F 2015/00636* (2013.01); *B01F 2015/0221* (2013.01); *G01N 1/38* (2013.01); *G01N 35/025* (2013.01); *G01N 2035/00514* (2013.01); *Y10T 436/25* (2015.01); *Y10T 436/25625* (2015.01)

(58) Field of Classification Search
None
See application file for complete search history.

(56) References Cited

U.S. PATENT DOCUMENTS 5,660,467 A    8/1997  Mineo et al.
6,875,401 B1 *    4/2005  Suzuki et al. ................... 422/63
(Continued)

FOREIGN PATENT DOCUMENTS

JP    57-99326 A    6/1982
JP    5-302928 A    11/1993
(Continued)

OTHER PUBLICATIONS

Software translation of Kato, S. et al. JP 2000-338113; Dec. 2000.*
(Continued)

*Primary Examiner* — Yelena G Gakh
*Assistant Examiner* — Michelle Adams
(74) *Attorney, Agent, or Firm* — Mattingly & Malur, PC

(57) ABSTRACT

In the field of automatic analyzers, as items to be analyzed are increase, various reagents differing in such properties as liquid viscosity and contact angle are being used more frequently, and this trend is expected to continue. Also, reagents now take various forms (e.g., a concentrated reagent to be diluted by the water of an automatic analyzer), and so does dilution water. Such being the case, the invention provides an automatic analyzer capable of sufficient stirring regardless of items to be analyzed. To sufficiently stir a substance to which a reagent has been added, the automatic analyzer is designed to alter stirring conditions after a given amount of time has passed since the addition of that reagent.

7 Claims, 8 Drawing Sheets

(51) Int. Cl.
  *B01F 7/16* (2006.01)
  *B01F 15/00* (2006.01)
  *B01F 15/02* (2006.01)
  *G01N 35/02* (2006.01)
  *G01N 35/00* (2006.01)

(56) References Cited

U.S. PATENT DOCUMENTS

| | | |
|---|---|---|
| 2001/0019702 A1 | 9/2001 | Watari et al. |
| 2003/0166260 A1 | 9/2003 | Katou et al. |
| 2008/0240992 A1 | 10/2008 | Murakami |

FOREIGN PATENT DOCUMENTS

| | | |
|---|---|---|
| JP | 7-253432 A | 10/1995 |
| JP | 08-192036 A | 7/1996 |
| JP | 08-233827 A | 9/1996 |
| JP | 9-145718 A | 6/1997 |
| JP | 2000-338113 A | 12/2000 |
| JP | 2001-124784 A | 5/2001 |
| JP | 2001-242176 A | 9/2001 |
| JP | 2003-33637 A | 2/2003 |
| JP | 2003-035715 A | 2/2003 |
| JP | 2003-121450 A | 4/2003 |
| JP | 2003-254981 A | 9/2003 |
| JP | 2005-99046 A | 4/2005 |
| JP | 2007-033414 A | 2/2007 |
| JP | 2007-108061 A | 4/2007 |
| WO | 99/46601 A1 | 9/1999 |
| WO | WO-2007/043261 A1 * | 4/2007 |

OTHER PUBLICATIONS

Software translation of Takahashi Katsuaki, JP 2003-121450, patent application published on Apr. 23, 2003.*
Japanese Office Action received in Japanese Application No. 2012-118141 dated Jan. 7, 2014.
Chinese Office Action received in corresponding Chinese Application No. 200980105566.8 dated Sep. 4, 2014.
Japanese Office Action received in corresponding Japanese Application No. 2014-246015 dated Sep. 8, 2015.

* cited by examiner

FIG.4

| | AMOUNT DISPENSED (μl) | VISCOSITY [mPa·s] | | CONTACT ANGLE [°] | |
|---|---|---|---|---|---|
| | | | AFTER STIRRING | | AFTER STIRRING |
| REAGENT | 20 | 1.00 | 1.00 | 15.0 | 20.0 |
| DILUTION WATER | 130 | 1.00 | | 100.0 | |

FIG.5

| STIRRING PARAMETERS | AMOUNT DISPENSED (μl) | VISCOSITY [mPa·s] | CONTACT ANGLE [°] | SEGMENT NO. | | | | | | | | | | VOLTAGE |
|---|---|---|---|---|---|---|---|---|---|---|---|---|---|---|
| | | | | 1 | 2 | 3 | 4 | 5 | 6 | 7 | 8 | 9 | 10 | |
| 501(CONVENTIONAL) | 150 | 1.00 | 20.0 | 0 | 0 | 0 | 0 | 1 | 1 | 1 | 0 | 0 | 0 | 5 |
| 502(NEW) | 150 | 1.00 | 100.0 | 0 | 0 | 0 | 0 | 1 | 1 | 1 | 0 | 0 | 0 | 3 |
| 501(NEW) | 150 | 1.00 | 20.0 | 0 | 0 | 0 | 0 | 1 | 1 | 1 | 0 | 0 | 0 | 5 |

AUTOMATIC ANALYZER

TECHNICAL FIELD

The present invention relates to automatic analyzers that perform qualitative and quantitative analyses of biological samples such as blood and urine and particularly to an automatic analyzer having means for stirring a biological sample and a reagent.

BACKGROUND ART

A typical automatic analyzer involves the process of adding a reagent, which reacts with a particular substance to be analyzed, to a sample and stirring them. After a given amount of reaction time, a photometer is used, in the case of a biochemical analysis, to measure changes in the absorbance of the reacted liquid; in the case of an immunoassay or gene analysis, an actinometer such as photomultiplier tube and the like is used to count labeled substances that have bound to the substance to be analyzed. Examples of stirring methods include contact stirring, in which a paddle-like stirrer is immersed in a substance to be stirred and rotates or makes a reciprocal motion to stir the substance, and non-contact stirring, in which sound waves are radiated toward a substance to be stirred.

Patent Document 1 discloses a technique for enhancing stirring efficiency. Specifically, the rotational speed and stirring time of a stirrer and the insertion amount of a rotary stirrer with respect to a substance to be stirred are altered based on analysis conditions such as the kinds and amounts of reagent and dilution water and dilution rates. Patent Document 2 also discloses a technique for enabling effective stirring. This technique is based on the consideration of the top-surface heights of substances to be stirred when contained in different reaction vessels as well as their dynamical characteristics such as viscosity, density, and surface tension.

PRIOR ART LITERATURE

Patent Document 1: JP-9-145718-A
Patent Document 2: JP-2005-99046-A

SUMMARY OF THE INVENTION

Problem to be Solved by the Invention

In the field of automatic analyzers, as items to be analyzed are increase, various reagents differing in such properties as liquid viscosity and contact angle are being used more frequently, and this trend is expected to continue. Also, reagents now take various forms (e.g., a concentrated reagent to be diluted by the water of an automatic analyzer), and so does dilution water. Accordingly, a conventional stirring method in which only one stirring condition is used to stir a reagent would fail to stir all such reagents sufficiently.

An object of the invention is thus to provide an automatic analyzer capable of sufficiently stirring a sample and a reagent inside a reaction vessel regardless of items to be analyzed.

Means for Solving the Problem

The above object of the invention is achieved by altering stirring conditions used for stirring a reagent after a given amount of time.

In one aspect, the invention is an automatic analyzer comprising: a plurality of paddle-like stirrers each of which is immersed in a substance to be stirred and rotates or makes a repetitive motion to stir the substance; and drive means for independently altering, based on items to be analyzed, the rotational speed and angle of each of the stirrers. To stir a substance including a reagent, this analyzer operates the drive means to alter the rotational speed and angle of each of the stirrers and performs stirring using two or more stirring conditions.

In another aspect, the invention is an automatic analyzer that stirs a substance by radiating sound waves toward the substance. To stir a substance including a reagent, this analyzer selects which electrode on a piezoelectric element to use and alters the intensity of the sound radiation.

Effect of the Invention

As described above, the invention is an automatic analyzer comprising: stirring means for stirring a mixed liquid including a sample and a reagent; and control means for controlling the stirring means such that the stirring means operates under two or more different stirring conditions when stirring the mixed liquid including the reagent. When the automatic analyzer has a physical stirrer, the analyzer alters the rotational speed and stirring time of the stirrer. When the analyzer has means for generating sound waves, the analyzer selects which electrode on a piezoelectric element to use and alters the intensity of the sound radiation. Such configurations allow sufficient stirring regardless of the items to be analyzed.

BRIEF DESCRIPTION OF THE DRAWINGS

FIG. 4 is an example of the liquid properties of a reagent and associated stirring parameters according to an embodiment of the invention;
FIG. 5 is an example of the liquid properties of a reagent and stirring conditions to be set for a stirring mechanism according to an embodiment of the invention.

MODE FOR CARRYING OUT THE INVENTION

Embodiments of the present invention will now be described with reference to the accompanying drawings.

Embodiment 1

Figure 1:
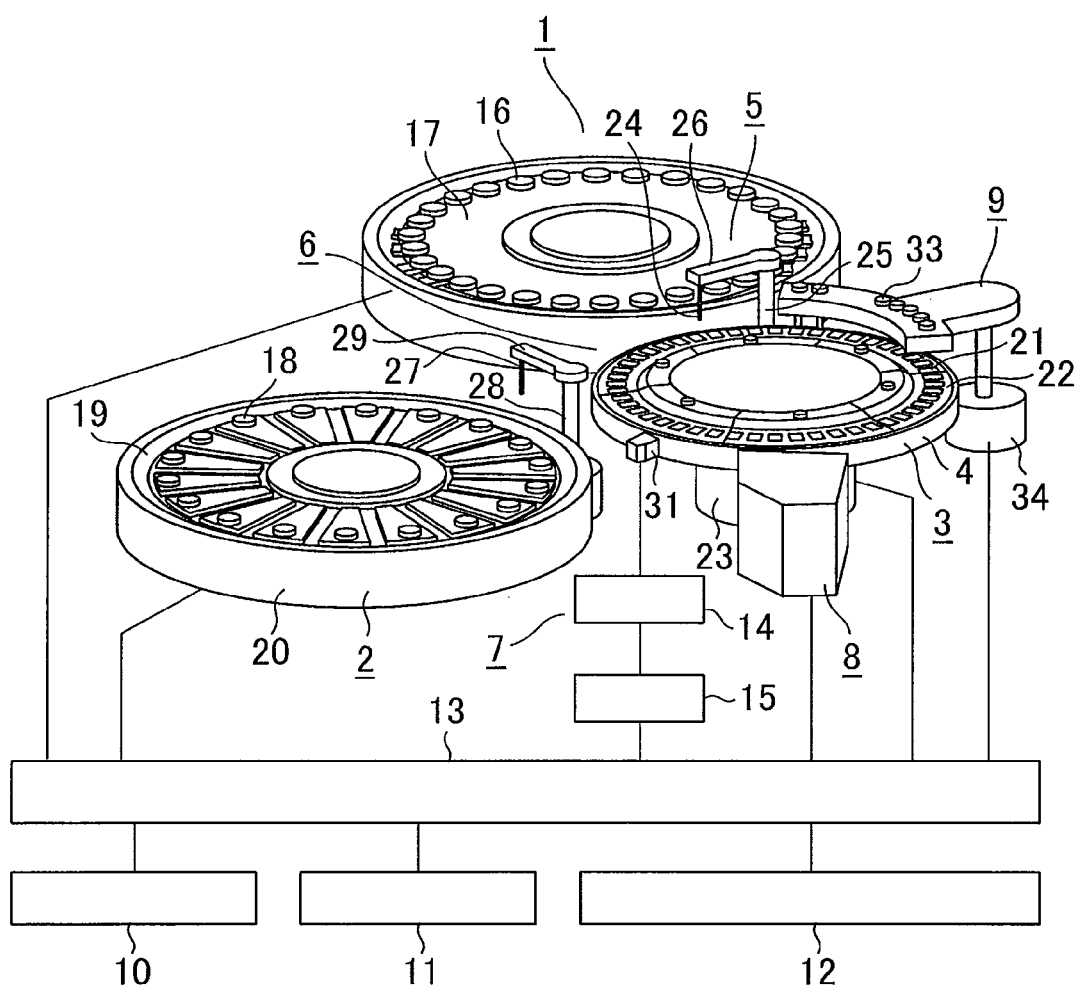
FIG. 1 is a perspective view illustrating the configuration of an automatic analyzer according to an embodiment of the invention.
Figure 2:
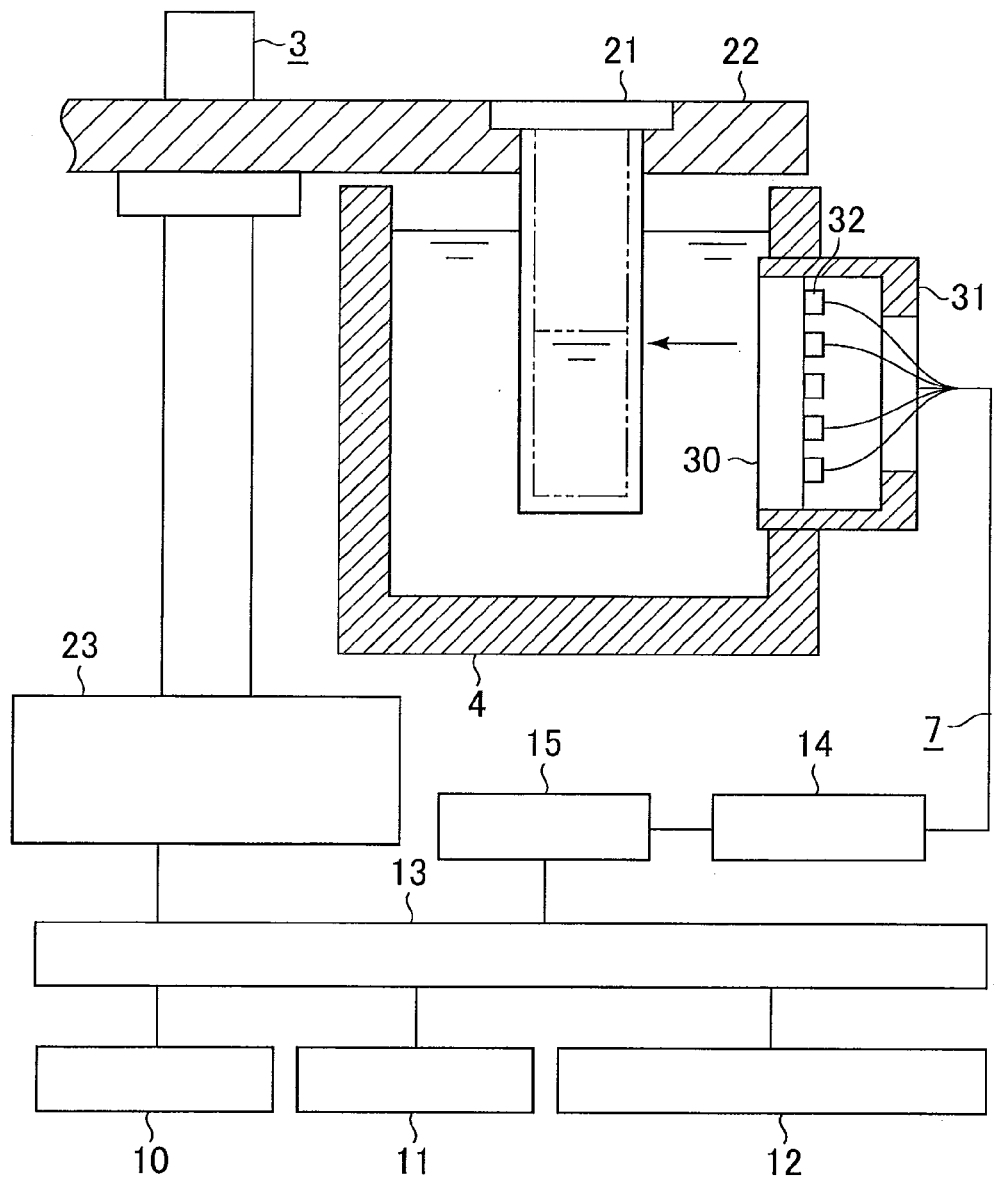
FIG. 2 is a cross section of an automatic analyzer according to an embodiment of the invention, particularly illustrating a stirring mechanism and its adjacent components.

FIG. 1 is a schematic illustrating an automatic analyzer representative of the invention, and the automatic analyzer comprises a stirring mechanism 7 that includes a piezoelectric element. FIG. 2 is a cross section of the automatic analyzer of FIG. 1, particularly illustrating the stirring mechanism 7 and its adjacent components.

As illustrated in FIG. 1, the automatic analyzer of Embodiment 1 comprises the following main components: a sample disk 1, a reagent disk 2, a reaction disk 3, a reaction bath 4, a sampling mechanism 5, a pipetting mechanism 6, the stirring mechanism 7, a photometric instrument 8, a rinsing mechanism 9, a display unit 10, an input unit 11, a storage unit 12, and a control unit 13. The sample disk 1 includes a circular disk 17, and multiple sample vessels 16 are arranged fixedly along the circumference the circular disk 17. The sample vessels 16 are each capable of containing a sample. A drive mechanism (not illustrated) including a motor, a rotary shaft, and the like is used to rotate the circular disk 17 in the circumferential direction so that the circular disk 17 can be located at any position. The reagent disk 2 includes a circular disk 19, and the circular disk 19 has multiple reagent bottles 18 arranged fixedly along its circumference. The reagent bottles 18 are each capable of containing a reagent, which is to be mixed with a sample for chemical reaction. The outer circumference of the circular disk 19 is covered with a temperature-controlled refrigeration wall 20. Similar to the circular disk 17, a drive mechanism (not illustrated) including a motor, a rotary shaft, and the like is used to rotate the circular disk 19 in the circumferential direction so that the circular disk 19 can be located at any position. The reaction disk 3 is equipped with multiple reaction-vessel holders 22, each adapted to hold a reaction vessel 21 used to contain a sample and a reagent. A drive mechanism 23 is used to alternate horizontal rotational movements and stops of the reaction disk 3 during a given cycle, thereby moving the reaction vessels 21 intermittently. The reaction bath 4 is located along the transfer path of the reaction vessels 21 and is a temperature-controlled tank in which constant-temperature water or the like maintains the temperatures of a reacted liquid contained in the reaction vessels 21 at a constant temperature so that chemical reactions between the samples and reagents can be promoted. The reaction vessels 21 move inside the reaction bath 4. The sampling mechanism 5 includes the following components: a sampling probe 24; a support shaft 25; an arm 26 attached to the support shaft 25; and a drive mechanism that allows the sampling probe 24 attached to the arm 26 to rotate about the support shaft 25 so that the sampling probe 24 can make reciprocal rotational movements between the sample disk 1 and the reaction disk 3. Following a particular analysis sequence, the sampling mechanism 5 dispenses the sample inside a sample vessel 16 into a reaction vessel 21 when the rotation of the sample disk 1 has moved that sample vessel 16 to a predetermined position. Similar to the sampling mechanism 5, the pipetting mechanism 6 includes the following components: a pipetting probe 27; a support shaft 28; an arm 29 attached to the support shaft 28; and a drive mechanism that allows the pipetting probe 27 attached to the arm 29 to rotate about the support shaft 28 so that the pipetting probe 27 can make reciprocal rotational movements between the reagent disk 2 and the reaction disk 3. Following a particular analysis sequence, the pipetting mechanism 6 dispenses the reagent inside a reagent bottle 18 into a reaction vessel 21 when the rotation of the reagent disk 2 has moved that reagent bottle 18 to a predetermined position. Note that the sample vessels 16 and the reagent bottles 18 can contain different samples and different reagents, respectively, and a reagent and a sample are supplied to a reaction vessel 21 as much as needed. The stirring mechanism 7 is designed to stir and mix the sample and reagent contained in a reaction vessel 21 when that reaction vessel 21 has been transferred to a stirring position. The stirring methods of the invention described hereinafter are advantageous regardless of which stirring scheme is to be used, contact stirring that involves the use of a physical stirrer or non-contact stirring that involves the use of ultrasonic waves or the like.

FIG. 2 is an example when the invention is applied to non-contact stirring. As illustrated in FIG. 2, the stirring mechanism 7 includes the following components: a fixed unit 31 that is fixed at a location where a side face of a reaction vessel 21 located at the stirring position can be irradiated with sound waves; a piezoelectric-element driver 14 that drives a piezoelectric element 30 (as shown in FIG. 2) and a stirring mechanism controller 15. The stirring mechanism controller 15 is connected to the control unit 13 and designed to drive the piezoelectric-element driver 14 as well as to control the entire operation of the stirring mechanism 7. The piezoelectric element 30, which acts as a sound source, is attached to the fixed unit 31 such that a side face of the piezoelectric element 30 is immersed in the constant-temperature water inside the reaction bath 4. The piezoelectric element 30 has multiple electrodes 32, and the piezoelectric-element driver 14 causes the piezoelectric element 30 to vibrate at a given frequency. A target position of sound radiation can be changed by the vibration of the electrodes 32. The photometric instrument 8 includes, though not illustrated in FIG. 1, a light source, a photometer, a lens, and a signal processor. The photometric instrument 8 is designed to perform photometric analysis of the properties of a sample by measuring, for example, the absorbance of the reacted liquid inside a reaction vessel 21. The rinsing mechanism 9 (see FIG. 1) includes multiple nozzles 33 and a vertical drive mechanism 34 for lifting or lowering the nozzles 33. When certain reaction vessels 21 have been transferred to rinsing positions, the rinsing mechanism 9 suctions reacted liquid out of those reaction vessels 21 and discharges rinsing liquid into the reaction vessels 21 to rinse them. The display unit 10 displays various data on its screen, ranging from items to be analyzed to analysis results, and the input unit 11 allows input of data such as the items to be analyzed or the like. The storage unit 12 is used to store various information, such as preset sequences (or programs) to control each component of the automatic analyzer and the items to be analyzed.

With reference again to FIG. 2, a reaction vessel 21 into which a sample and a reagent have been dispensed is secured to the reaction disk 3 by a reaction-vessel holder 22. When the reaction disk 3 rotates in the circumferential direction, the reaction vessel 21 also moves in the constant-temperature water inside the reaction bath 4. After reaching the stirring position, the reaction vessels 21 comes to a halt, and the piezoelectric-element driver 14 then starts to vibrate the piezoelectric element 30 at a given frequency. The vibration of the piezoelectric element 30 propagates through the constant-temperature water inside the reaction bath 4 as sound waves, reaching a side surface of the reaction vessel 21. These sound waves pass through the side surface of the reaction vessel 21 and consequently reach the sample and reagent inside the reaction vessel 21 to stir them. The vibrational waves that have propagated into the reaction vessels 21 act on the vapor-liquid interfaces of the sample and reagent, causing swirling flows. These swirling flows work to stir the sample and reagent.

Discussed next is the operation of the above-described automatic analyzer.

When the rinsing mechanism 9 has rinsed a reaction vessel 21 and the reaction disk 3 has transferred the reaction vessel 21 to the sample injection position on the reaction disk 3, the sample disk 1 begins to rotate so as to transfer a sample vessel 16 that contains a sample to the sampling position on the sample disk 1. The reagent disk 2 also rotates to transfer a particular reagent bottle 18 to the pipetting position on the reagent disk 2.

Subsequently, the sampling mechanism 5 is activated for the sampling probe 24 to dispense the sample of the sample vessel 16, now located at the sampling position, into the reaction vessel 21, now located at the sample injection position. After the sample has been injected to the reaction vessel 21, the reaction vessel 21 is transferred from the sample injection position to the reagent injection position on the reaction disk 3. The pipetting mechanism 6 is then activated to dispense the reagent of the reagent bottle 18, now located at the pippeting position on the reagent disk 2, into the reaction vessel 21, now located at the reagent injection position.

Thereafter, the reaction vessel 21 is transferred to the stirring position, where the stirring mechanism 7 stirs the sample and reagent inside the reagent vessel 21.

The resultant mixture stirred inside the reagent vessel 21 is measured by the photometric instrument 8 in terms of absorbance while the reaction vessel 21 passes between the light source and photometer of the photometric instrument 8. This measurement is performed during a few cycles, and the reaction vessel 21 is rinsed by the rinsing mechanism 9 after the completion of the measurement.

The analysis by the automatic analyzer of Embodiment 1 further proceeds by performing such a series of operations as above for each reagent vessel 21.

Discussed next are the distinctive features of Embodiment 1 during the stirring by the stirring mechanism 7.

In Embodiment 1, the stirring mechanism 7 determines the target position and intensity of sound radiation as instructed by the control unit 13 by the time a reaction vessel 21 is transferred to the stirring position. Selection of which electrode 32 to use and the determination of the sound radiation intensity are done based on the amount and properties of the liquid contained in the reaction vessel 21; specifically, these are done by searching a stirring parameter table stored by the storage unit 12 for specific parameters to be used for stirring the liquid. During the stirring operation, the electrode selection and the sound radiation intensity are altered after the passage of a given amount of time so that the stirring operation can be performed in a phased manner.

Figure 3:
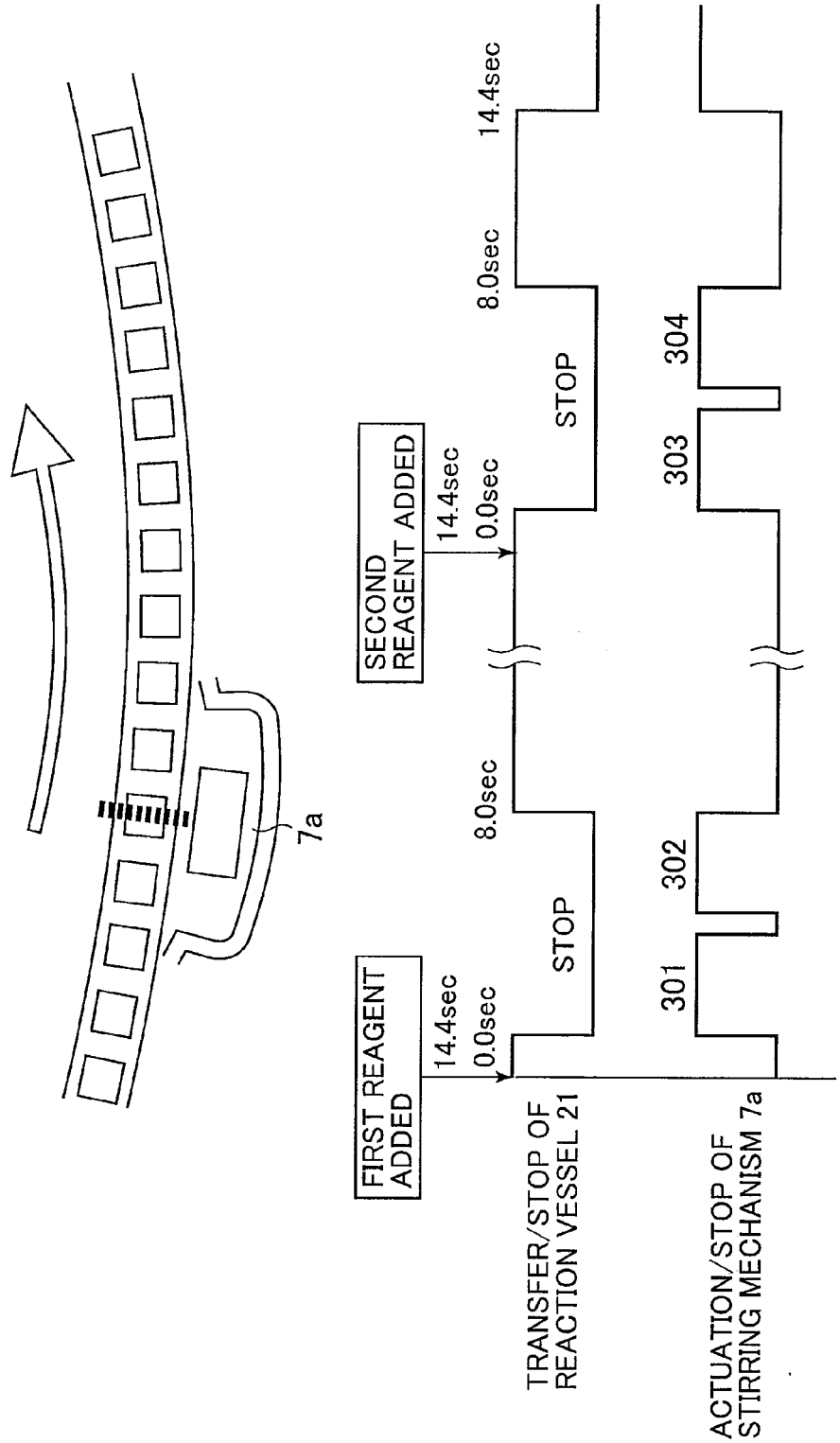
FIG. 3 is an operational example of a stirring mechanism of an automatic analyzer according to an embodiment of the invention.

When an automatic analyzer has low throughput, a sufficient amount of time is often allocated for a single stirring operation. In that case, the stirring operation can be performed by assigning two or more sets of stirring parameters to a single stirrer. FIG. 3 is an example in which the stirring mechanism 7 of Embodiment 1 has a single stirrer 7a and two sets of stirring parameters are assigned to the stirrer 7a. When a reaction vessel 21 containing a sample and a first reagent is transferred to the stirring position which is located in front of the stirrer 7a, the reaction vessel 21 comes to a halt, followed by activation of the stirrer 7a. The stirring parameters to be used at this time are first stirring parameters 301, which are the parameters to be used after the addition of the first reagent. After the passage of a given amount of time, a stirring operation is performed again with the use of stirring parameters 302, not the first stirring parameters 301. A few minutes later, a second reagent is added to the liquid inside the reaction vessel 21. As in the addition of the first reagent, when the reaction vessel 21, now containing the sample and the first and second reagents, is transferred to the stirring position in front of the stirrer 7a, the reaction vessel 21 comes to a halt, followed by activation of the stirrer 7a. The stirring parameters to be used at this time are first stirring parameters 303, which are the parameters to be used after the addition of the second reagent. Thereafter, the first stirring parameters 303 are replaced by stirring parameters 304 to perform a stirring operation again. FIGS. 4 and 5 are an example showing alteration of stirring parameters. Assume here that a concentrated reagent is used for analysis and that the contact angle of the reagent is much smaller than that of dilution water. FIG. 4 shows the hypothetical liquid properties of the reagent, and FIG. 5 shows stirring parameters for stirring the reagent and the dilution water. FIG. 5 is based on the assumptions that the piezoelectric element 30 is divided into ten segments, with the uppermost segment being 'No. 1' and that a voltage to be applied (i.e., sound radiation intensity) can be adjusted according to a scale of 1 to 10, with the largest voltage being '1.' As a conventional parameter setting, FIG. 5 shows stirring parameters 501 which are suitable for the amount and liquid properties of the mixture made up of the dilution water and reagent. In this case, the sound radiation intensity is 5 or a middle value. However, as shown in FIG. 4, the ratio of the dilution water amount to the reagent amount is 13 to 2, meaning the dilution water is much larger in amount. Thus, in such a case as above, or when dilution water and a reagent are not sufficiently mixed right after the addition of the reagent, the stirring parameters 502 of FIG. 5 should be adopted, which parameters are suitable for the liquid properties of the dilution water. As the stirring parameters 502 indicates, its sound radiation intensity is 3 and relatively high. After the first-time sound radiation with the use of the stirring parameters 502, it is then possible to adopt the stirring parameters 501, which are suitable for the liquid properties of the mixture, because the dilution water and the reagent have been completely mixed. As already stated, the stirring parameters 501 are conventional ones. It is also possible to use different segments of the piezoelectric element 30 by considering liquid viscosity even if the same amount of liquid is to be used.

When using two or more reagents which differ considerably in terms of liquid properties, it is possible to perform electrode reselection and alteration of the sound radiation intensity after the passage of a given amount of time, thereby achieving effective stirring.

Figure 6:
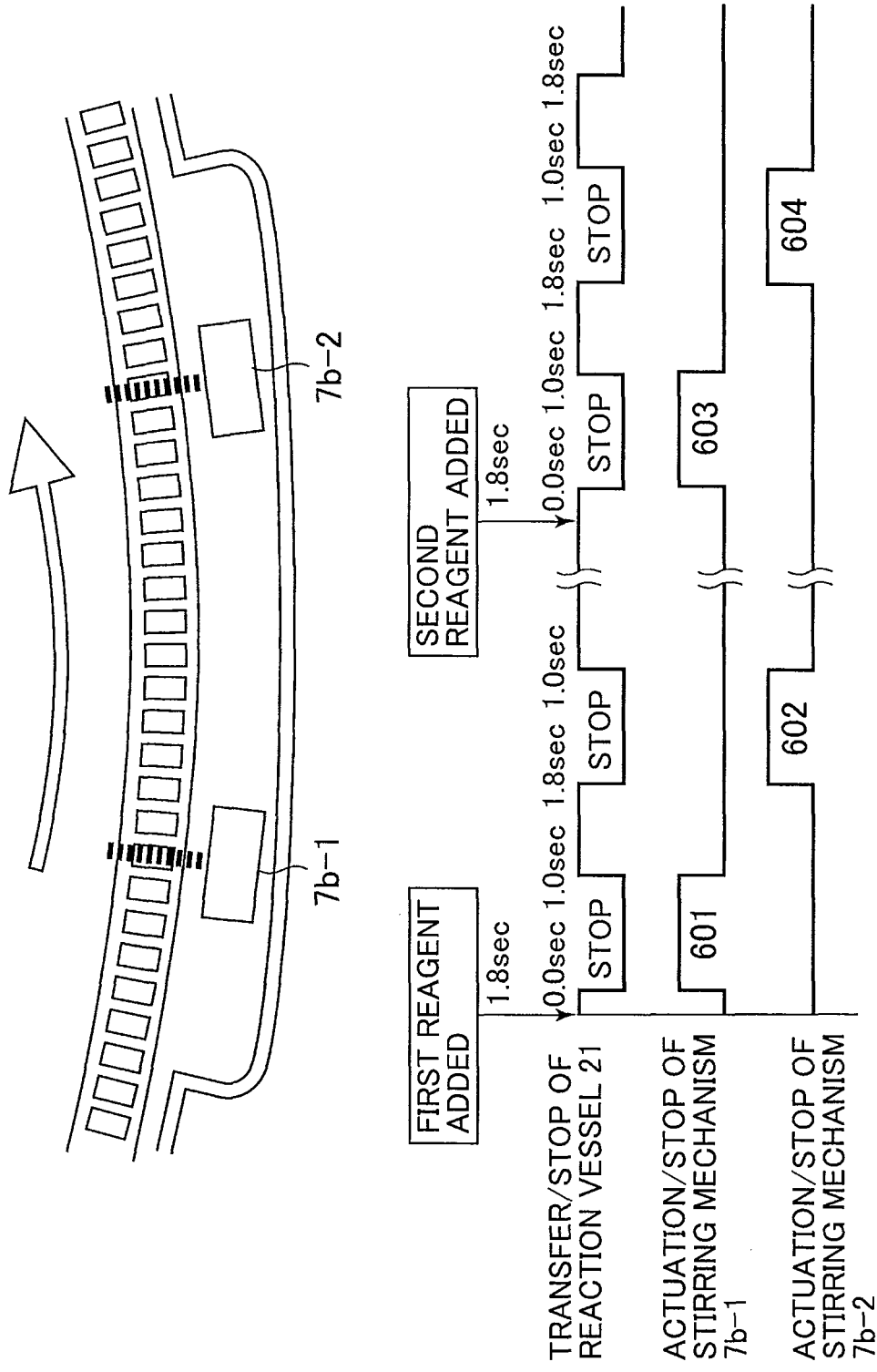
FIG. 6 is an operational example of a stirring mechanism of an automatic analyzer according to an embodiment of the invention.

When an automatic analyzer has high throughput, a sufficient amount of sound radiation time is often not allocated for a single stirring operation. Accordingly, it is often the case that the automatic analyzer is equipped with multiple stirrers. FIG. 6 is an example in which the stirring mechanism 7 of Embodiment 1 has multiple stirrers 7b-1 and 7b-2 and different sets of stirring parameters are assigned to the stirrers 7b-1 and 7b-2. When a reaction vessel 21 containing a sample and a first reagent is transferred to the stirring position located in front of the stirrer 7b-1, the reaction vessel 21 comes to a halt, and the stirrer 7b-1 then starts to operate based on stirring parameters 601. After the stirring by the stirrer 7b-1, the reaction vessel 21 is transferred to the stirring position located in front of the stirrer 7b-2 and comes to a halt, and the stirrer 7b-2 then starts to operate based on stirring parameters 602. A few minutes later, a second reagent is added to the liquid inside the reaction vessel 21. As in the addition of the first reagent, when the reaction vessel 21, now containing the sample and the first and second reagents, is transferred to the stirring position in front of the stirrer 7b-1, the reaction vessel 21 is subjected to stirring by the stirrer 7b-1 based on stirring parameters 603. The reaction vessel 21 is then transferred to the stirring position in front of the stirrer 7b-2 and subjected to stirring by the stirrer 7b-2 based on stirring parameters 604.

As described above, the use of two different sets of stirring parameters for a single reagent leads to sufficient stirring.

Figure 7:
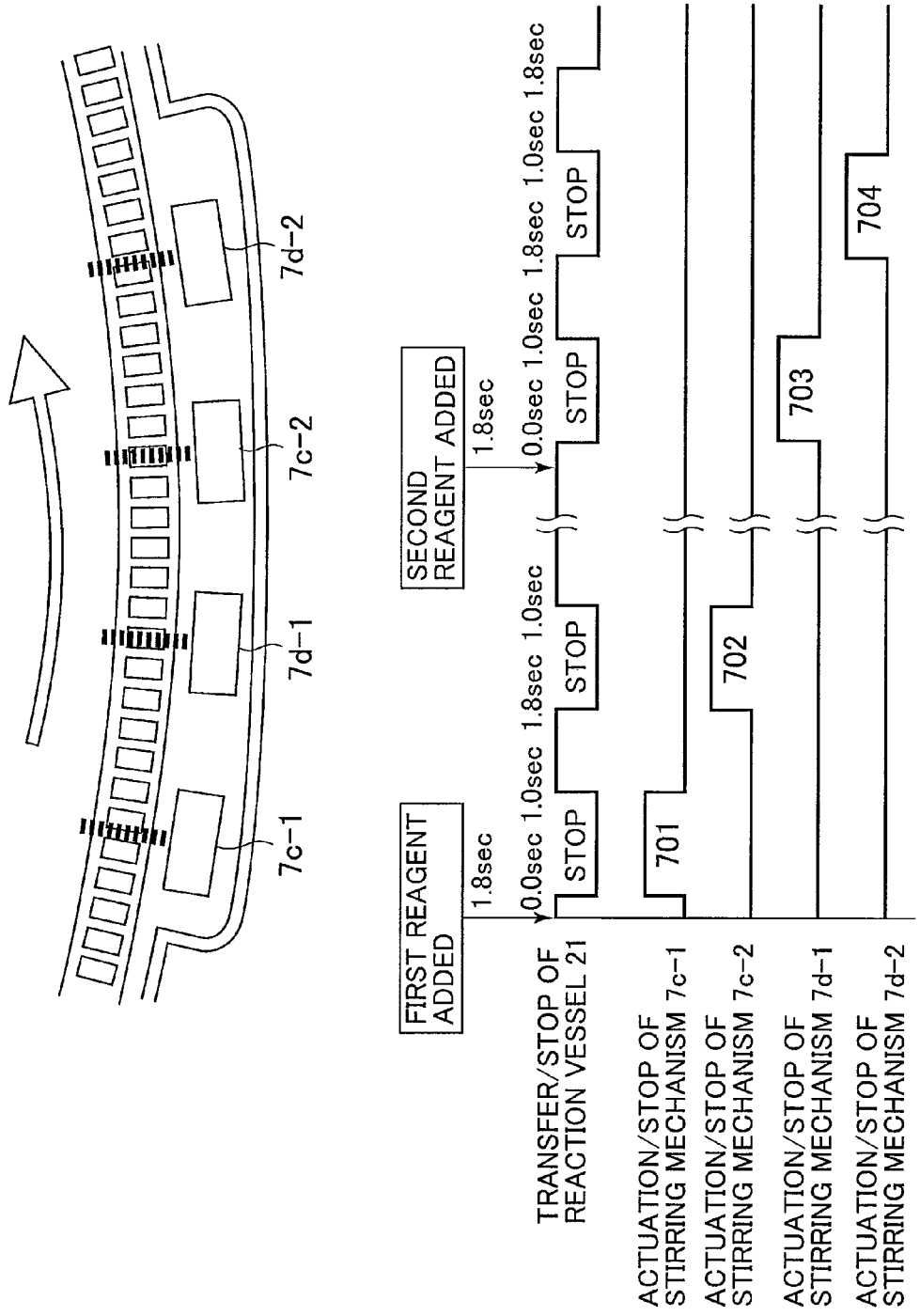
FIG. 7 is an example of how to functionally expand a stirring mechanism of an automatic analyzer according to an embodiment of the invention.

When an automatic analyzer has even higher throughput, more stirrers can be used. Assume, for example, that in an analysis involving the use of two reagents, different stirrers are to be used for the first and second reagents. In that case, the stirring mechanism 7 can be functionally expanded as illustrated in FIG. 7. After the addition of the first reagent, a stirrer 7c-1 performs stirring based on stirring parameters 701, and a stirrer 7c-2 then performs stirring based on stirring parameters 702. After the addition of the second reagent, a stirrer 7d-1 performs stirring based on stirring parameters 703, and a stirrer 7d-2 then performs stirring based on stirring parameters 704.

Figure 8:
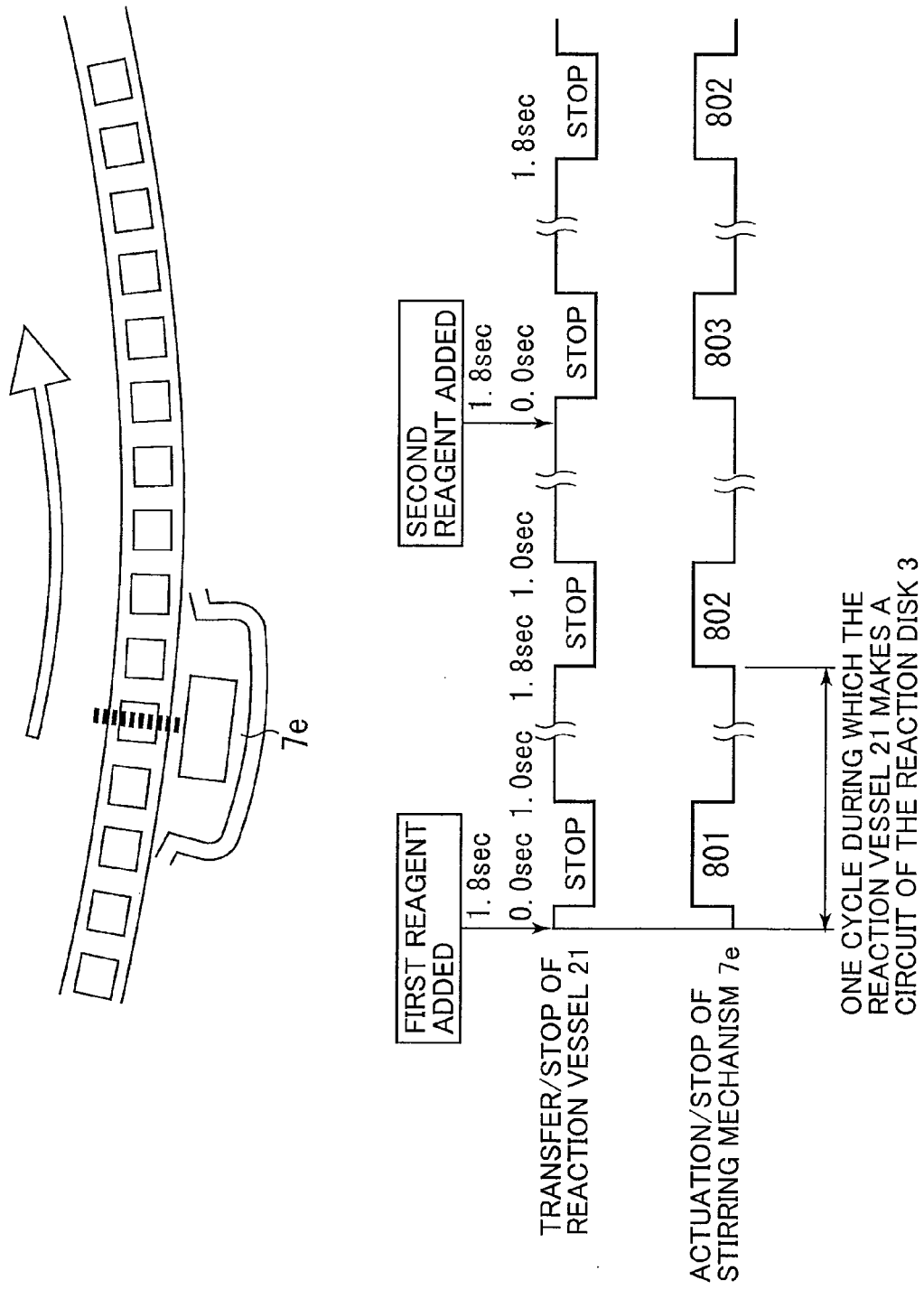
FIG. 8 is an example of how to functionally expand a stirring mechanism of an automatic analyzer according to an embodiment of the invention.

FIG. 8 illustrates another embodiment of the invention in which photometric analysis is performed after multiple cycles of reaction-vessel transfers and stops. If an automatic analyzer with high throughput is reduced in size, it is likely that the analyzer may be unable to have multiple stirrers. In such a case where only one stirrer exists, associated problems can be solved by radiating sound waves toward a reaction vessel every time the vessel passes the stirrer so that the liquid inside the vessel can be stirred sufficiently and by performing photometric analysis thereafter. Specifically, after the addition of a first reagent, a stirrer 7e performs stirring on a reaction vessel 21 based on stirring parameters 801. Because there is not much time to switch the stirring parameters 801 to different ones during the single stirring operation, multiple cycles of transfers and stops of the reaction vessel 21 are repeated until the reaction vessel 21 rotates around. When the reaction vessel 21 is transferred again to the stirring position in front of the stirrer 7e, the stirrer 7e performs stirring based on stirring parameters 802. After the addition of a second reagent, the stirrer 7e performs stirring based on stirring parameters 803. Then, after one rotation of the reaction vessel 21, the stirrer 7e performs stirring based on stirring parameters 804.

Figure 9:
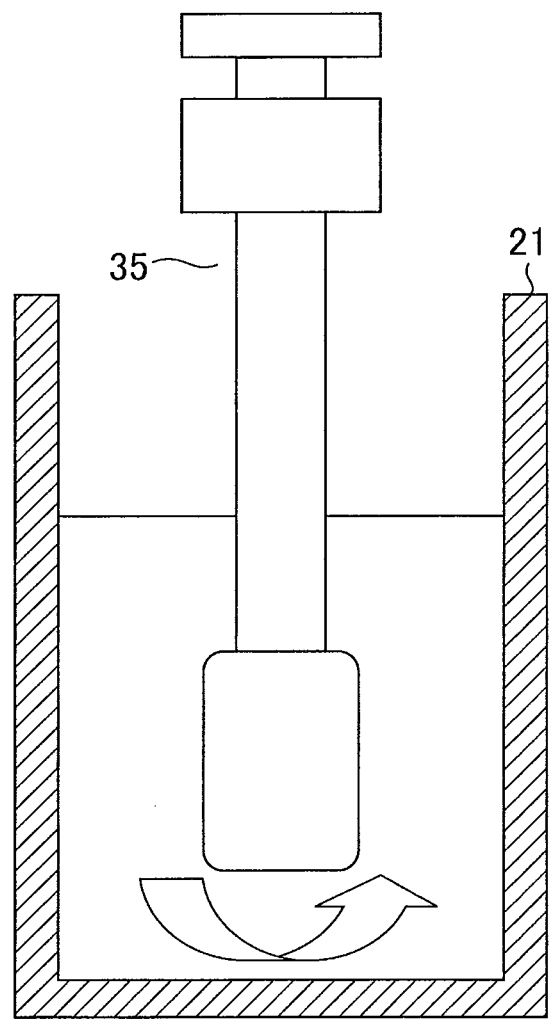
FIG. 9 is a cross section of a stirring mechanism of an automatic analyzer according to an embodiment of the invention.

FIG. 9 schematically illustrates a physical stirrer to be used for contact stirring. As in non-contact stirring, the use of the physical stirrer also leads to effective stirring by altering, after the passage of a given amount of time, stirring conditions according to reagents to be added. Assume here that the hypothetical reagent and dilution water of FIG. 4 are to be stirred with the physical stirrer while altering stirring parameters. In that case, too, the example of the stirring parameter alteration of FIG. 5 can be applied. In stirring the hypothetical reagent and dilution water of FIG. 4, stirring parameters conventionally adopted are the stirring parameters 501 of FIG. 5, which are suitable for the amount and liquid properties of the mixture made up of the dilution water and reagent. In this case, the stirring speed of the physical stirrer is medium. However, as shown in FIG. 4, the ratio of the dilution water amount to the reagent amount is 13 to 2, meaning the dilution water is much larger in amount. Thus, in such a case as above, or when dilution water and a reagent are not sufficiently mixed right after the addition of the reagent, the stirring parameters 502 of FIG. 5 should be adopted, which parameters are suitable for the liquid properties of the dilution water. The stirring speed of the physical stirrer in this case is set higher than when the stirring parameters 501 are used. After a given amount of stirring time based on the stirring parameters 502, it is then possible to adopt the stirring parameters 501, which have the medium stirring-speed parameter and are suitable for the liquid properties of the mixture, because the dilution water and the reagent have been completely mixed. As already stated, the stirring parameters 501 are conventional ones. In addition to the stirring speed, such parameter alternation can further include alteration of stirring time and of the insertion amount of the physical stirrer with respect to a liquid to be stirred.

As stated above, alteration of stirring parameters after the passage of a given amount of time enables sufficient stirring regardless of the types of automatic analyzer or of the items to be analyzed.

DESCRIPTION OF REFERENCE NUMERALS

1: Sample disk
2: Reagent disk
3: Reaction disk
4: Reaction bath
5: Sampling mechanism
6: Pipetting mechanism
7: Stirring mechanism
8: Photometric instrument
9: Rinsing mechanism
10: Display unit
11: Input unit
12: Storage unit
13: Control unit
14: Piezoelectric-element driver
15: Stirring controller
16: Sample vessel
17, 19: Circular disk
18: Reagent bottle
20: Refrigeration wall
21: Reaction vessel
22: Reaction-vessel holder
23: Drive mechanism
24, 27: Probe
25, 28: Support shaft
26, 29: Arm
30: Piezoelectric element
31: Fixed unit
32: Electrode
33: Nozzle
34: Vertical drive mechanism
35: Stirrer
301: First stirring parameters after the addition of a first reagent in the case of a single stirrer
302: Second stirring parameters after the addition of a first reagent in the case of a single stirrer
303: First stirring parameters after the addition of a second reagent in the case of a single stirrer
304: Second stirring parameters after the addition of a second reagent in the case of a single stirrer
501: Conventional stirring parameters
502: First stirring parameters after the addition of a reagent
601: First stirring parameters after the addition of a first reagent in the case of two stirrers
602: Second stirring parameters after the addition of a first reagent in the case of two stirrers
603: First stirring parameters after the addition of a second reagent in the case of two stirrers
604: Second stirring parameters after the addition of a second reagent in the case of two stirrers
701: First stirring parameters after the addition of a first reagent in the case of four stirrers
702: Second stirring parameters after the addition of a first reagent in the case of four stirrers
703: First stirring parameters after the addition of a second reagent in the case of four stirrers
704: Second stirring parameters after the addition of a second reagent in the case of four stirrers 801: First stirring parameters used after the addition of a first reagent when an automatic analyzer has high throughput but has only one stirrer 802: Second stirring parameters used after the addition of a first reagent when an automatic analyzer has high throughput but has only one stirrer 803: First stirring parameters used after the addition of a second reagent when an automatic analyzer has high throughput but has only one stirrer 804: Second stirring parameters used after the addition of a second reagent when an automatic analyzer has high throughput but has only one stirrer

The invention claimed is:

1. An automatic analyzer, comprising:
a control unit;
a first stirring mechanism, having a plurality of first electrodes, configured to stir a mixed liquid including a sample, a reagent, and dilution water contained in a reaction container;
a second stirring mechanism, having a plurality of second electrodes, configured to stir the mixed liquid in the reaction container;
a reaction disk configured to hold the reaction container at a predetermined position on the reaction disk;
a drive mechanism configured to rotate the reaction disk; and
a storage unit configured to store a first stirring intensity condition, which are parameters indicating one or more of the first electrodes that are enabled and a voltage applied to the one or more first electrodes that are enabled, and a second stirring intensity condition, which are parameters indicating one or more of the second electrodes that are enabled and a voltage applied to the one or more second electrodes that are enabled,
wherein the control unit is programmed to receive the first stirring intensity condition and the second stirring intensity condition from the storage unit,
wherein the control unit is programmed to control the drive mechanism to rotate the reaction disk so the predetermined position holding the reaction container is moved to a first position in front of the first stirring mechanism,
wherein the control unit is programmed to control the first stirring mechanism according to the first stirring intensity condition,
wherein the control unit is programmed to control the drive mechanism to rotate the reaction disk so the predetermined position holding the reaction container is moved to a second position in front of the second stirring mechanism,
wherein the control unit is programmed to control the second stirring mechanism according to the second stirring intensity condition,
wherein the first stirring intensity condition is different than the second stirring intensity condition, and
wherein the control unit is programmed to select the first stirring intensity condition from a set of possible first stirring intensity conditions based on data indicating an amount of the dilution water in the reaction container, and the control unit is programmed to select the second stirring intensity condition from a set of possible second stirring intensity conditions based on data of properties of the mixed liquid having been stirred by the first stirring mechanism.

2. The automatic analyzer of claim 1,
wherein the control unit is programmed to control the first stirring mechanism according to the first stirring intensity condition for a first predetermined amount of time, and
wherein the control unit is programmed to control the second stirring mechanism according to the second stirring intensity condition for a second predetermined amount of time.

3. The automatic analyzer of claim 1,
wherein the reagent in the mixed liquid is a reagent of a plurality of reagents held in a reagent disk,
wherein the control unit is programmed to select the first stirring intensity condition from the set of first stirring intensity conditions based on properties of the reagent in the mixed liquid, which are stored in the storage unit for each of the plurality of reagents.

4. The automatic analyzer of claim 1,
wherein the first stirring mechanism includes a first piezoelectric element having the plurality of first electrodes disposed on the first piezoelectric element,
wherein the second stirring mechanism includes a second piezoelectric element having the plurality of second electrodes disposed on the second piezoelectric element, and
wherein the control unit is programmed to select the first stirring intensity condition from the set of possible first stirring intensity conditions and the second stirring intensity condition from the set of possible second stirring intensity conditions based on data indicating a viscosity and data indicating an amount of the mixed liquid.

5. The automatic analyzer according to claim 1,
wherein the voltage applied to the one or more first electrodes that are enabled in the first stirring intensity condition is greater than the voltage applied to the one or more second electrodes that are enabled in the second stirring intensity condition.

6. An automatic analyzer, comprising:
a control unit;
a first stirring mechanism, having a plurality of first electrodes to stir a mixed liquid including a sample and a reagent contained in a reaction container;
a second stirring mechanism, having a plurality of second electrodes, configured to stir the mixed liquid in the reaction container;
a reaction disk configured to hold the reaction container at a predetermined position on the reaction disk;
a drive mechanism configured to rotate the reaction disk; and
a storage unit configured to store a first stirring intensity condition, which are parameters indicating one or more of the first electrodes that are enabled and a voltage applied to the one more first electrodes that are enabled, and a second stirring intensity condition, which are parameters indicating one or more of the second electrodes that are enabled and a voltage applied to the one or more second electrodes that are enabled,
wherein the control unit is programmed to receive the first stirring intensity condition and the second stirring intensity condition from the storage unit,
wherein the control unit is programmed to control the drive mechanism to rotate the reaction disk so the predetermined position holding the reaction container is moved to a first position in front of the first stirring mechanism,
wherein the control unit is programmed to control the first stirring mechanism according to the first stirring intensity condition for a predetermined amount of time, wherein the control unit is programmed to control the drive mechanism to rotate the reaction disk so the predetermined position holding the reaction container is moved to a second position in front of the second stirring mechanism, wherein the control unit is programmed to control the second stirring mechanism according to the second stirring intensity condition, wherein the first stirring intensity condition is different than the second stirring intensity condition, and wherein the control unit is programmed to select the first stirring intensity condition from a set of possible first stirring intensity conditions based on data indicating an amount of the dilution water in the reaction container, and the control unit is programmed to select the second stirring intensity condition from a set of possible second stirring intensity conditions based on data of properties of the mixed liquid having been stirred by the first stirring mechanism.

7. An automatic analyzer, comprising:

a control unit;

a first ultrasonic stirrer, having a plurality of electrodes, to stir a mixed liquid including a sample, a reagent and dilution water contained in a reaction container;

a second ultrasonic stirrer, having a plurality of second electrodes, configured to stir the mixed liquid in the reaction container;

a reaction disk configured to hold the reaction container at a predetermined position on the reaction disk;

a drive mechanism configured to rotate the reaction disk; and a storage unit configured to store a first stirring intensity, which are parameters indicating one or more of the first electrodes that are enabled and a voltage applied to the one or more first electrodes that are enabled, and a second stirring intensity condition, which are parameters indicating one or more second electrodes that are enabled and a voltage applied to the one or more second electrodes that are enabled, wherein the control unit is programmed to receive the first stirring intensity condition and the second stirring intensity condition from the storage unit, wherein the control unit is programmed to control the drive mechanism to rotate the reaction disk so the predetermined position holding the reaction container is moved to a first position in front of the first ultrasonic stirrer, wherein the control unit is programmed to control the first ultrasonic stirrer according to the first stirring intensity condition, wherein the control unit is programmed to control the drive mechanism to rotate the reaction disk so the predetermined position holding the reaction container is moved to a second position in front of the second ultrasonic stirrer, wherein the control unit is programmed to control the second ultrasonic stirrer according to the second stirring intensity condition, wherein the first stirring intensity condition is different than the second stirring intensity condition, and wherein the control unit is programmed to select the first stirring intensity condition from a set of possible first stirring intensity conditions based on data indicating an amount of the dilution water in the reaction container, and the control unit is programmed to select the second stirring intensity condition from a set of possible second stirring intensity conditions based on data of properties of the mixed liquid having been stirred by the first ultrasonic stirrer.

* * * * *